United States Patent
Choi et al.

(10) Patent No.: US 9,554,832 B2
(45) Date of Patent: Jan. 31, 2017

(54) APPARATUS AND METHOD FOR DIRECT VERTEBRAL ROTATION

(71) Applicant: Stryker Spine, Cestas (FR)

(72) Inventors: Andy Wonyong Choi, Wayne, NJ (US); Michael L. Schmitz, Roswell, GA (US); Se-il Suk, Nowon-Gu (KR)

(73) Assignee: Stryker European Holdings I, LLC, Kalamazoo, MI (US)

( * ) Notice: Subject to any disclaimer, the term of this patent is extended or adjusted under 35 U.S.C. 154(b) by 0 days.

(21) Appl. No.: 13/889,847

(22) Filed: May 8, 2013

(65) Prior Publication Data

US 2013/0245694 A1 Sep. 19, 2013

Related U.S. Application Data

(62) Division of application No. 12/152,834, filed on May 16, 2008, now Pat. No. 8,465,529.

(60) Provisional application No. 60/930,770, filed on May 18, 2007.

(51) Int. Cl.
*A61B 17/70* (2006.01)

(52) U.S. Cl.
CPC ......... *A61B 17/7074* (2013.01); *A61B 17/708* (2013.01); *A61B 17/7077* (2013.01)

(58) Field of Classification Search
CPC .................................. A61B 17/7074–17/708
USPC ....................................................... 606/86 A
See application file for complete search history.

(56) References Cited

U.S. PATENT DOCUMENTS

| | | | |
|---|---|---|---|
| 5,219,349 A | 6/1993 | Krag et al. | |
| 5,281,223 A | 1/1994 | Ray | |
| 5,478,340 A | 12/1995 | Kluger | |
| 6,090,113 A | 7/2000 | Le Couedic et al. | |
| 6,287,250 B1 | 9/2001 | Peng et al. | |
| 6,511,484 B2 | 1/2003 | Torode et al. | |
| 6,554,831 B1 | 4/2003 | Rivard et al. | |
| 6,565,568 B1 | 5/2003 | Rogozinski | |
| 6,610,009 B2 * | 8/2003 | Person | 600/234 |

(Continued)

FOREIGN PATENT DOCUMENTS

| | | |
|---|---|---|
| FR | 2757761 A1 | 7/1998 |
| JP | 10014934 A | 1/1998 |

(Continued)

OTHER PUBLICATIONS

Depuy Spine, Vertebral Body Derotation Surgical Technique.

(Continued)

*Primary Examiner* — Nicholas Plionis
(74) *Attorney, Agent, or Firm* — Lerner, David, Littenberg, Krumholz & Mentlik, LLP

(57) ABSTRACT

An instrument for spinal rotation that aligns and holds direct vertebral rotation (DVR) lever arms relative to each other to achieve an initial axial alignment of a segment of vertebrae and allows the final DVR rotation by rotating the instrument and lever arms together. A method of direct vertebral rotation that allows rotating the vertebrae to be aligned relative to each other, and collectively rotating the vertebrae to be aligned relative to adjacent spinal segments by rotating the direct vertebral rotation instrument. A system for direct vertebral rotation having at least two pedicle screws. The system also includes at least two levers attachable to the pedicle screws and a clamping instrument configured to clamp the levers.

14 Claims, 5 Drawing Sheets

(56) References Cited

U.S. PATENT DOCUMENTS

| | | | |
|---|---|---|---|
| 6,620,174 B2 * | 9/2003 | Jensen et al. | 606/130 |
| 6,875,211 B2 | 4/2005 | Nichols et al. | |
| 6,964,665 B2 | 11/2005 | Thomas et al. | |
| 8,608,746 B2 | 12/2013 | Kolb et al. | |
| 2002/0161368 A1 | 10/2002 | Foley et al. | |
| 2002/0174759 A1 | 11/2002 | Bernardelle et al. | |
| 2003/0065328 A1 | 4/2003 | Shevtsov et al. | |
| 2004/0172057 A1 * | 9/2004 | Guillebon et al. | 606/207 |
| 2005/0033291 A1 | 2/2005 | Ebara | |
| 2005/0245928 A1 | 11/2005 | Colleran et al. | |
| 2006/0149236 A1 | 7/2006 | Barry | |
| 2006/0195092 A1 | 8/2006 | Barry | |
| 2006/0200132 A1 | 9/2006 | Chao et al. | |
| 2006/0271050 A1 | 11/2006 | Piza Vallespir | |
| 2007/0142785 A1 | 6/2007 | Lundgaard et al. | |
| 2007/0162031 A1 * | 7/2007 | Hogg et al. | 606/79 |
| 2007/0213715 A1 | 9/2007 | Bridwell et al. | |
| 2007/0213716 A1 * | 9/2007 | Lenke | A61B 17/025 606/264 |
| 2010/0100133 A1 | 4/2010 | Carl et al. | |

FOREIGN PATENT DOCUMENTS

| | | |
|---|---|---|
| JP | 2005169064 A | 6/2005 |
| JP | 2008537900 A | 10/2008 |
| WO | 2006096516 A2 | 9/2006 |
| WO | 2006104813 A2 | 10/2006 |

OTHER PUBLICATIONS

Extended European Search Report for Application No. EP08767770 dated Feb. 28, 2013.

International Search Report issued in connection with corresponding International Appln. No. PCT/US08/06330.

Medtronic, CD Horizon Legacy Spinal System; With Vertebral Column Manipulation (VCM) Instrument Set; Advanced Deformity Correction Surgical Technique.

Extended European Search Report for Appln. No. EP15187397 dated Mar. 7, 2016.

Lee, et al., Direct Vertebral Rotation: A New Technique of Three-Dimensional Deformity Correction With Segmental Pedicle Screw Fixation in Adolescent Idiopathic Scoliosis, SPINE vol. 29, No. 3, pp. 343-349, 2004, Lippincott Williams & Wilkins Inc.

* cited by examiner

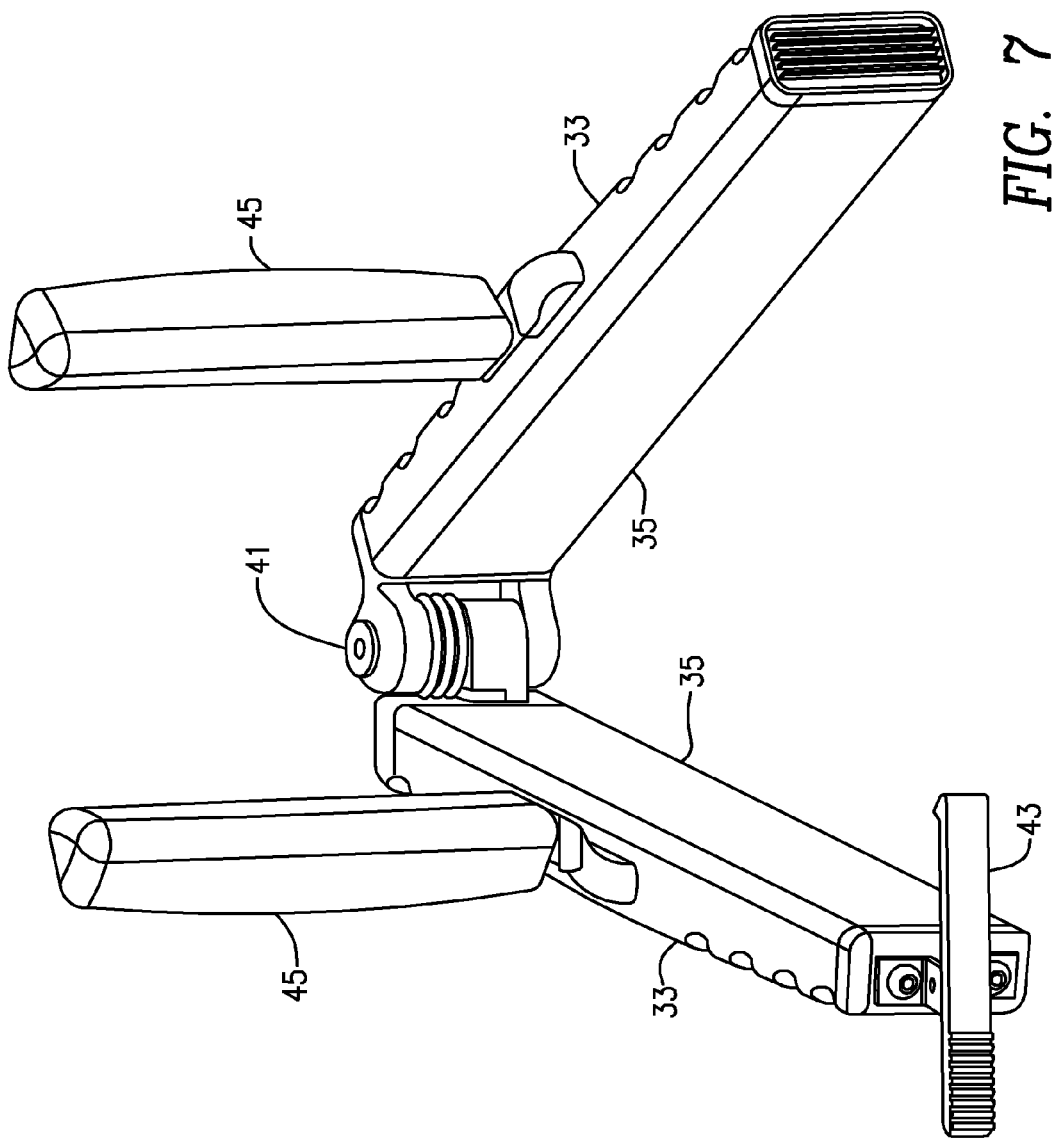

APPARATUS AND METHOD FOR DIRECT VERTEBRAL ROTATION

CROSS-REFERENCE TO RELATED APPLICATIONS

This application is a divisional application of U.S. application Ser. No. 12/152,834, filed on May 16, 2008, which claims the benefit of the filing date of U.S. Provisional Patent Application No. 60/930,770, filed May 18, 2007, the disclosures of which are hereby incorporated herein by reference.

FIELD OF THE INVENTION

The present invention relates generally to an alignment linkage such as a direct vertebral rotation instrument for creating, restraining and/or maintaining horizontal rotation of the vertebrae during posterior spinal fusion operations. The present invention also relates to a method for creating, restraining and/or maintaining horizontal rotation of the vertebrae during posterior spinal fusion operations.

BRIEF DESCRIPTION OF THE PRIOR ART

During spine surgery for conditions such as scoliosis, the surgeon seeks to achieve a three-dimensional correction of the spinal column shape by realigning and instrumenting the vertebrae in order to achieve an eventual fusion of the vertebral bodies in the desired alignment. Typically, the misalignment of the patient's vertebral bodies is readily apparent in the sagittal and coronal planes, either visually or by radiography. More difficult to see and correct is rotational misalignment of the vertebrae about the axis in the defined along the length of the spine. This rotation is often characterized in the scoliosis patient by projection of the ribs of the back creating a so-called rib hump on one side of the back caused by the rotation of the thoracic vertebrae and the attached ribs. While the axis of rotation actually changes along the length of the spine due to the spines natural curvature, for convenience of discussion the axis will be discussed as if it is a vertical line.

In order to correct such a rotational misalignment, the surgeon must axially rotate the vertebrae in the opposite direction so that they are correctly oriented about the longitudinal axis of the spine. A corrective rotation of this type is often referred to as a "derotation."

Direct vertebral rotation, hereinafter "DVR," is one method of horizontally rotating and re-aligning vertebral bodies. To use DVR, screws are implanted in the pedicles of the vertebrae and then a horizontal torque is applied by a lever arm or extension tube mounted to the screw head. As mentioned above, the indication is frequently scoliosis, but other deformity issues may be addressed through DVR. Tubular lever arms are then placed on the screws in line with the axis of the screw. A force is then applied to the lever arms to rotate the spinal vertebrae. This brings the vertebrae into the desired positions and in line with one another. The surgeon and the surgeon's assistants face the difficult task of manually rotating and aligning the various lever arms to eventually fasten the pedicle screw assemblies to rods and form a construct holding the vertebrae in the desired alignment.

Polyaxial pedicle screw assemblies have, by way of example, a cage shaped to receive a bone screw, a rod and a blocker or set screw engaging screw threads. Generally, cages have two arms that extend away from the screw and define a slot through which the rod can pass transverse to the axis of the cage. Often, such cages are referred to as tulip shaped. The cage can move polyaxially about the head of the bone screw until the assembly is fixed in a position. Once the rod is in place, the blocker is threaded within or on the outside of the cage. The blocker engages, directly or indirectly, the rod which in turn engages the head of the bone screw seated in the cage or engages the cage itself. The blocker thus locks or immobilizes the assembly.

A monoaxial pedicle screw assembly generally includes a bone screw with an integral cage or head to receive the rod and blocker or nut.

For DVR, the lever arms apply torque to the bone screw and the bone screw, in turn, applies the torque to the vertebrae. Either a polyaxial or monoaxial screw assembly may be used. The lever must fit tightly and grasp the screw head in order to apply the torque. If a polyaxial screw assembly is used, the head should be immobilized in the direction of axial rotation to allow the transmission of torque. A polyaxial screw also has a limited extent of free travel and can create torque on the vertebra once the range of movement of the head is exceeded.

SUMMARY OF THE INVENTION

The present invention fills the need described above by providing a system and method for rotation of vertebral segments for posterior spinal fusion.

The invention is directed to an instrument and associated method that aligns and holds the DVR lever arms relative to each other to achieve an initial axial alignment of a segment of vertebrae and allow the DVR rotation by rotating the instrument and lever arms together.

Joining the lever arms or extension tubes with such a clamping instrument allows the surgeon to more uniformly and easily rotate the tubes together and to stepwise achieve a relative orientation of a segment of vertebrae. The segment of vertebra to be aligned can be aligned collectively relative to adjacent spinal segments.

In one aspect the invention teaches a method of direct vertebral rotation, wherein the steps include attaching pedicle screws to at least two vertebrae to be aligned and attaching a lever to each of the pedicle screws. The levers are positioning between jaws of a direct vertebral rotation instrument and the jaws held in closed position. The jaws are brought together to rotate the vertebrae to be aligned relative to each other, and the vertebrae to be aligned are collectively rotated relative to adjacent spinal segments by rotating the direct vertebral rotation instrument.

In another aspect the invention teaches a direct vertebral rotation instrument comprising a first jaw; a second jaw; a hinge connecting the first jaw and the second jaw; and a lock for locking the first jaw to the second jaw.

In yet another aspect the invention teaches a system for direct vertebral rotation having at least two pedicle screws. The system also includes at least two levers attachable to the pedicle screws and a clamping instrument configured to clamp the levers.

In one aspect of the present invention, the instrument has substantially parallel jaws to engage or clamp the lever arms in relative alignment for manipulation.

In another aspect of the invention, the jaws of the instrument have a compliant material for interface with the lever arms in order to assist in gripping the lever arms and thus facilitate the effective adjustment of the longitudinal position of the lever arms.

A further aspect of the invention includes the method of rotating vertebrae located within a patient's body about the spinal axis by: implanting a first pedicle screw on a first vertebra; implanting a second pedicle screw on a second vertebra; attaching a first moment arm and a second moment arm to the first screw and the second screw, respectively; locking the first moment arm and a second moment arm in a preliminary angular orientation with respect to the spinal axis by applying pressure using the opposing jaws of an instrument to align and restrain said moment arms; and rotating the instrument, arms and vertebra relative to the spinal axis.

The present invention may be reduced to practice by a clamping instrument which includes elongate jaws having opposed interior faces and being hingeably or rotatably connected at one end or interior from one end, the jaws having an open position and a closed position, the open position facilitating the instrument to be arranged about a plurality of pedicle screw extension tubes or other lever arms associated with vertebra. The instrument in its closed position holds and initially aligns the lever arms on the interior faces of the jaws.

In another aspect of the present invention, the above described instrument includes handles to facilitate at least the closing of the jaws. The handles may be in the central area of the jaws and extend transverse to the elongate axis of the jaws, or may be displaced towards or at one end of the jaws, or even as an extension generally in alignment with the elongate axis of the jaws, or a portion of the jaws themselves may serve as portions of handles.

In another aspect of the present invention, the jaws are hingeably connected at one end or are located interiorly from one end and include a spring mechanism to hold the jaws in a normally open position. This normally open position facilitates arrangement of the jaws about the extension tubes or lever arms to be clamped within the jaws. The hinge may be integral with one or both jaws, or may be a separate element connected to the jaws.

In another aspect of the present invention, the closing mechanism is provided to hold the jaws in a closed position such that a surgeon or surgeon's assistant does not need to hold the handles together in order to maintain the instrument in a closed position. In one embodiment, a closing mechanism may be a latching mechanism provided anywhere along the jaws, or even on the handles themselves. In a preferred embodiment, a latching mechanism is provided at the end of the jaws opposite the hinge mechanism, and comprises a pawl and ratchet arrangement which automatically latches the jaws as the jaws are closed. The latching mechanism may have an extension with a finger grip, which may simply be a surface designed to facilitate gripping of one's finger (knurling, raised gripping ribs, etc.). The finger gripping portion may extend laterally outside of one of the jaws such that a depression on that portion will release the pawl and ratchet mechanism.

In another aspect of the present invention, the interior faces of the jaws have a surface to facilitate gripping the extension tubes or lever arms. In a preferred embodiment, this may be a compliant material such as rubber. The coefficient of friction of such a material should facilitate the gripping of the lever arms, and the material may also include compliancy such that the lever arms are, upon undergoing a clamping force, forced into the material for gripping purposes. The compliance also allows the lever arms to be gripped at various angles and positions along the length of the jaws.

In another aspect of the present invention, a method includes the use of the above broadly described instrument by surrounding a plurality of lever arms with a normally open instrument, positioning the instrument about the lever arms, closing the instrument such that the jaws clamp the lever arms, and manually applying a torque and otherwise manipulating the instrument in order to manipulate the lever arms and thus the vertebra to which the lever arms are connected, directly or indirectly. The clamping of the jaws may achieve an initial desired alignment of the lever arms and vertebrae and then the entire assembly of the lever arms and vertebrae may be further rotated to the final position. The method may also include the steps of fixing spinal rods or other fixation devices arranged with respect to the vertebra to maintain the vertebra in the aligned position, and subsequently releasing the clamping instrument and removing the same from the lever arms.

BRIEF DESCRIPTION OF THE DRAWINGS

FIG. 7 is a perspective view of an instrument according to the present invention in the open position.

DETAILED DESCRIPTION OF THE PREFERRED EMBODIMENTS

Figure 1:
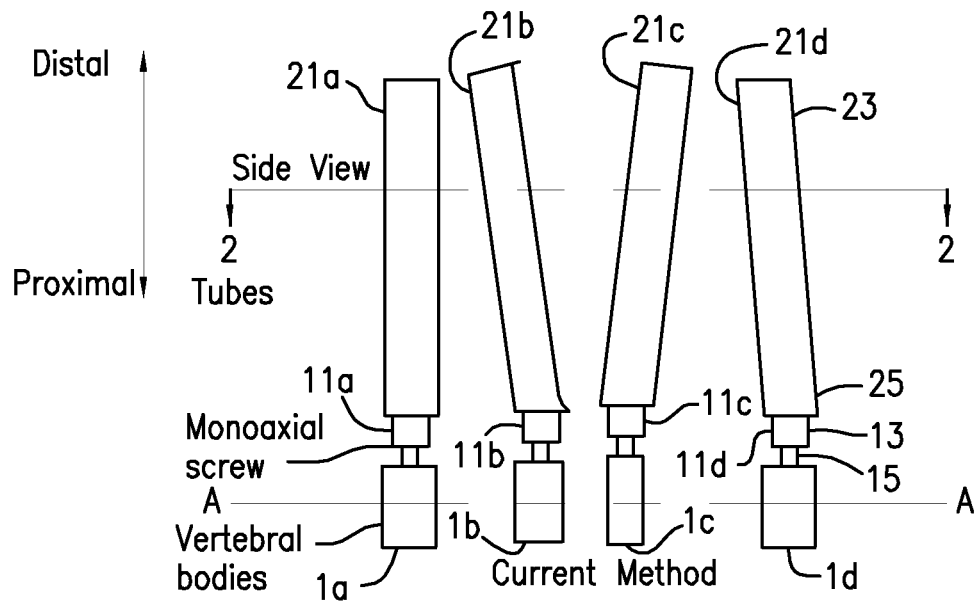
FIG. 1 is a schematic right side view of four adjacent vertebrae of a spine, with pedicle screws and lever arms as used in DVR.

Referring to FIG. 1, the portion of the spine illustrated includes a first vertebra 1a, which may be the T10 (Tenth Thoracic) vertebra of a patient, a second vertebra 1b, which may be the T9 (Ninth Thoracic) vertebra of a patient, a third vertebra 1c, which may be the T8 (Eighth Thoracic) vertebra of a patient, and a fourth vertebra 1d, which may be the T7 (Seventh Thoracic) vertebra of a patient. The systems and methods described hereafter may be applicable to any vertebra or vertebrae of the spine and/or the sacrum (not shown). In this application, the term "vertebra" may be broadly interpreted to include the sacrum although rotation is only attempted relative to the sacrum and the sacrum itself is not rotated.

Pedicle screw assemblies 11a-11d (collectively screws 11) are implanted in the associated pedicles of the vertebrae 1a-1d. In one of many pedicle screw arrangements, pedicle screw assemblies 11a-11d each have a cage 13 shaped to receive a rod and a set screw that passes through an aperture of the cage. Each screw 11 also has a threaded shaft 15 which is threaded into the vertebra 1 to implant the pedicle screw assembly.

Connected to the head 13 of each screw 11 are moment arms 21a-21d (collectively moment arms 21). In this embodiment the moment arms 21 are cannulated tubes having an open distal end 23 allowing placement of objects such as the aforementioned locking screws and suitable locking screw drivers through the cannulae of the tubes. These moment arms 21 serve as lever arms in connection with the vertebral rotation system herein. The proximal end 25 of each moment arm 21 removeably engages the head 13 of the respective pedicle screw assembly 11 so as to be able to apply torque to the vertebrae 1.

Figure 2:
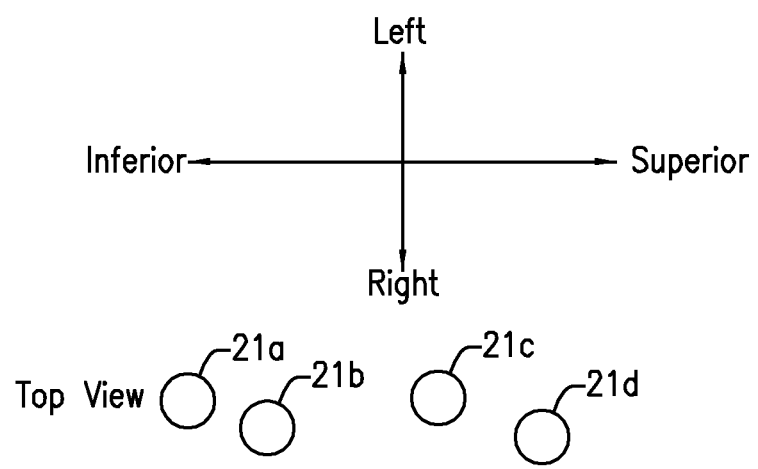
FIG. 2 is a plan view as in FIG. 1 showing the lever arms and establishing a coordinate system relative to the human body.

FIG. 2 shows a top view, related to FIG. 1, of the distal end of the moment arms 21a-21d. Also shown is a coordinate system defining superior and inferior directions along the spinal axis and left and right directions in the plane defined by the spine axis A-A. Thus, the torque to be applied by the moment arms 21 is in the left or right direction. It can be seen that the distal ends 23 of the moment arms 21 are offset in various left-right and inferior-superior directions depending on the initial geometry of the patient's spine and the pedicle screw placements as determined by the surgeon.

Figure 3:
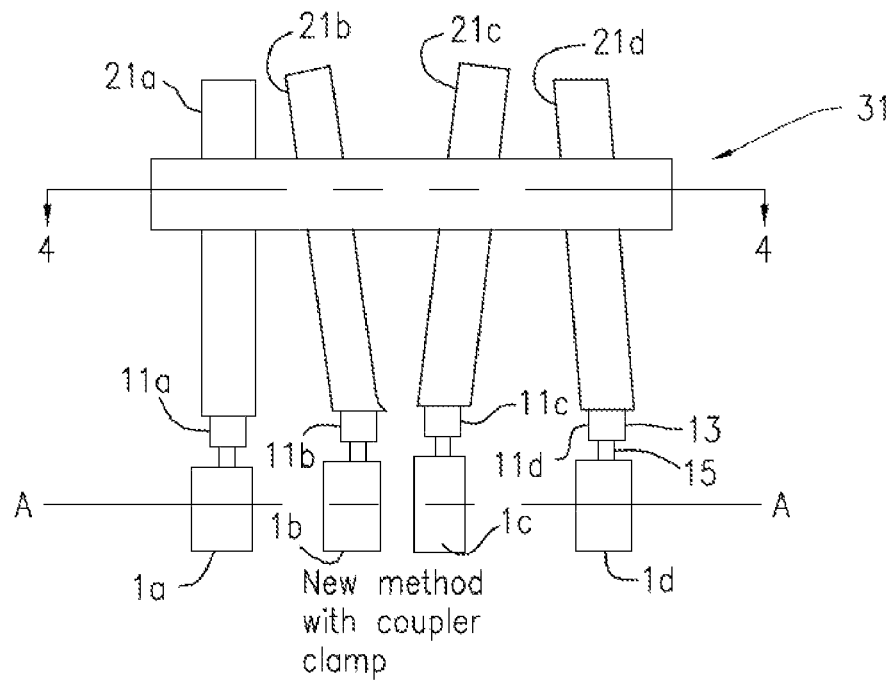
FIG. 3 is a schematic right side view of four adjacent vertebrae of a spine, with pedicle screws, lever arms and an instrument according to the present invention.

FIG. 3 schematically illustrates an embodiment of a clamping instrument 31 according to the present invention. The instrument 31 engages, aligns and restrains the positions of the moment arms 21 by clamping the arms 21 in the distal region outside the patient's body.

Figure 4:
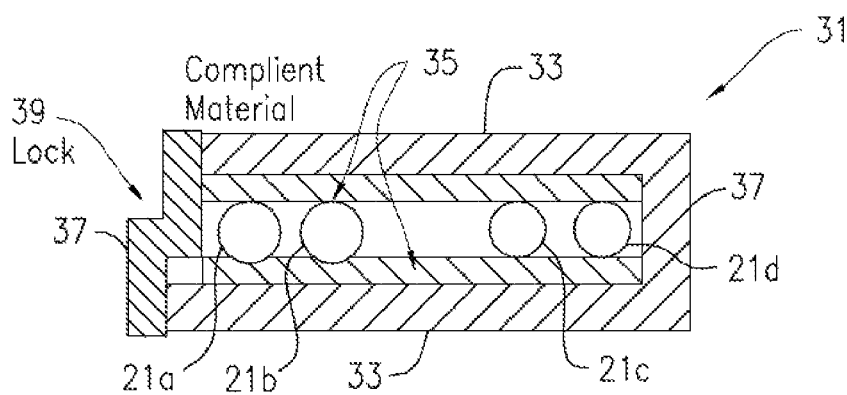
FIG. 4 is a plan view as in FIG. 3 showing the lever arms and instrument of the present invention.

FIG. 4 shows a top schematic view, related to FIG. 3, of the distal end of the moment arms 21a-21d and of the clamping instrument 31. The instrument 31 has longitudinal jaws 33 that are capable of being moved toward and away from each other in the lateral left and right directions to clamp onto the moment arms 21 and consequently align and restrain them. Each jaw 33 has a compliant material 35, such as a polymer or rubber, to conform to each moment arm 21 and accept the arms at various inferior-superior angles along the length of the jaws 35. The compliant material assists in gripping the moment arms 21.

End portions 37 of the clamping instrument 31 connect the jaws 33 to complete an approximately rectangular structure having a central opening for the moment arms 21. A first end portion 37 incorporates a hinge or other mechanism for allowing the jaws to come together and a second end portion 37 incorporates, in the preferred embodiment, a latching mechanism or other closing mechanism that restrains the jaws 33 in the closed position. The clamping instrument 31, once closed on the moment arms 21, are capable of being moved toward and away from each other in the lateral left and right directions to align and restrain the moment arms 21.

The clamping instrument 31 has two different functions for aligning the vertebrae. The first alignment is achieved by the closing and latching of the jaws 33 as shown by the relative rotations of the moment arms 21 shown between FIGS. 2 and 4. Thus, moment arm 21b is rotated leftward relative to arm 21a, moment arm 21c rightward relative to arm 21b and so on. Consequently, each vertebra is rotated relative to adjacent vertebrae to achieve an initial rotation within the instrumented segment of vertebrae. If straight moment arms 21 are used, the degree of initial rotation for each vertebra 1 depends primarily on the positioning and orientation of each pedicle screw assembly 11. If desired, a special moment arm 21 with an offset distal portion may be used to increase or decrease the preliminary rotation of a given vertebra 1.

The second alignment is achieved by manually rotating the clamping instrument 31 and the clamped moment arms 21 together to align the instrumented spinal segment. Thus, the clamping instrument 31 can achieve rotation both on a vertebra-to-vertebra basis and of an entire segment of the spine relative to the rest of the spine.

Figure 5:
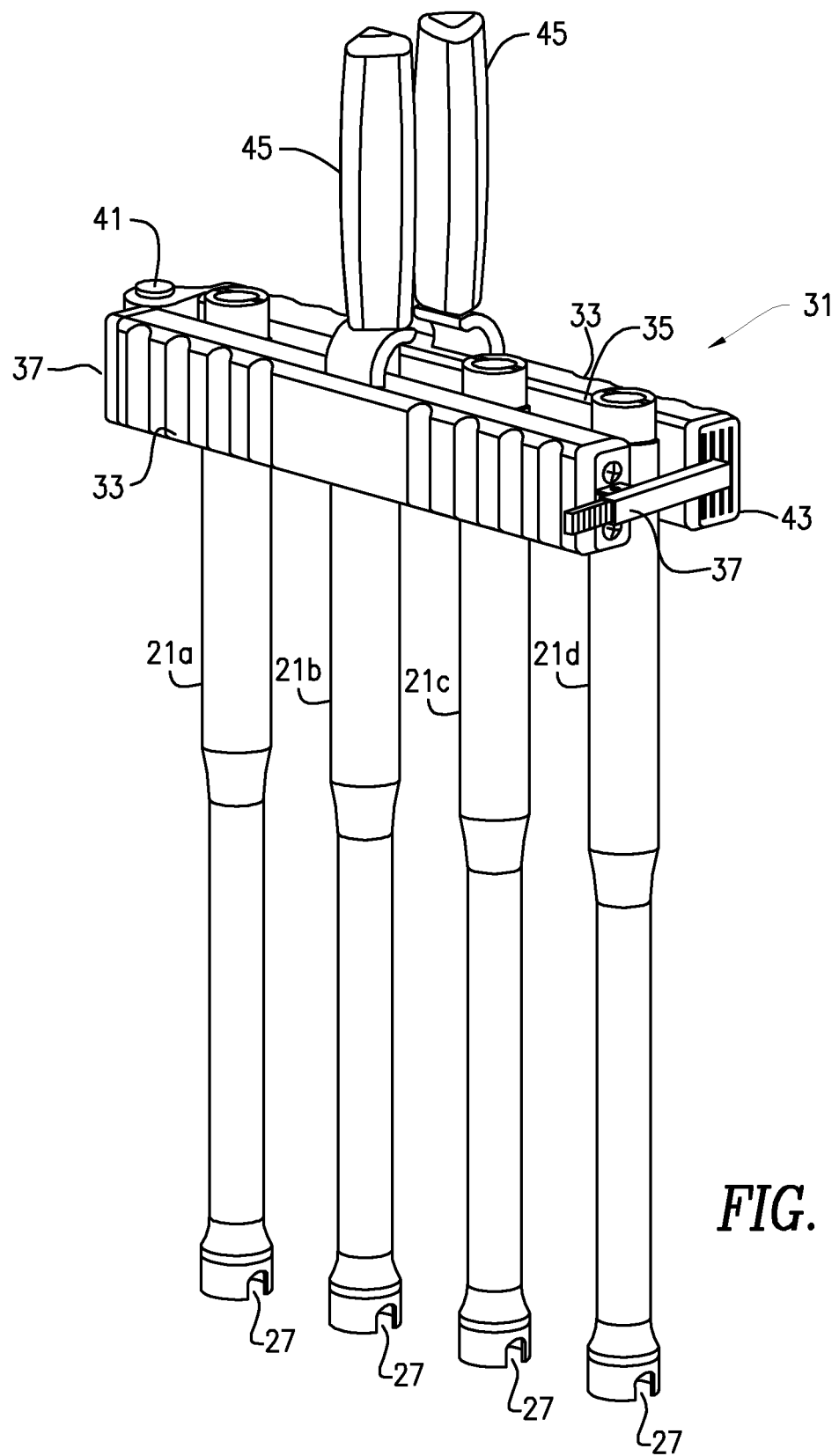
FIG. 5 is a perspective left side view of four lever arms and an instrument according to the present invention.

FIG. 5 shows a perspective view of a preferred embodiment of the invention with the clamping instrument 31 restraining four moment arms 21, each of which has a passage 27 at its proximal end to accommodate a spinal rod. Mounted to the longitudinal jaws 33 are handles 45. The handles 45 serve the dual purposes of assisting in the closing of the jaws for the initial rotation and then allowing manipulation of the entire instrument for the final rotation. The handles 45 may be placed in any suitable position on the clamping instrument 31. In the illustrated embodiment, the handles 45 are shown in a central location, but in other embodiments these may be closer to or at the latch end opposite the hinge end.

Figure 6:
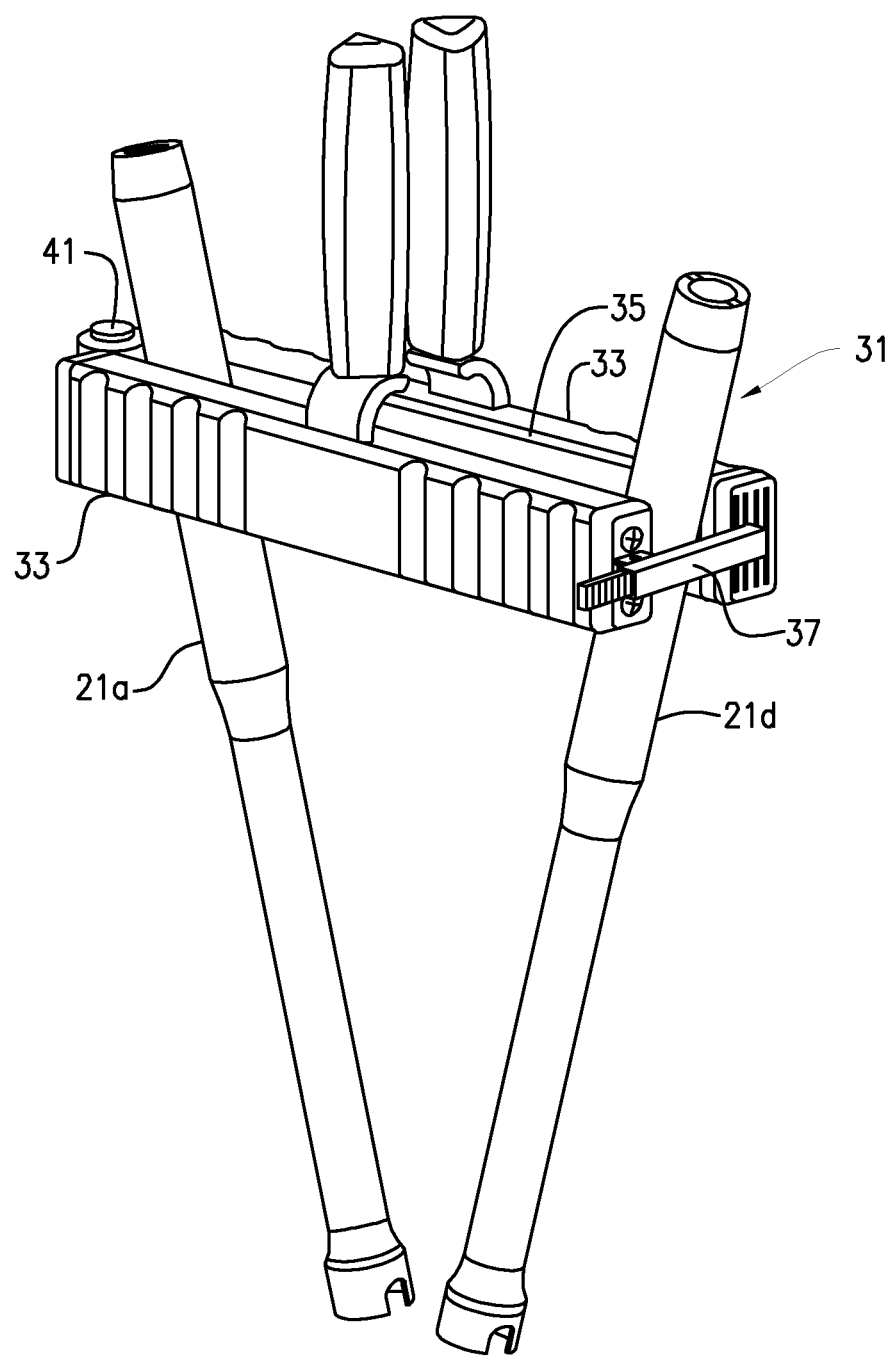
FIG. 6 is a perspective left side view of two lever arms and an instrument according to the present invention.

As also seen in FIG. 6, hinge 41 is at one end of the clamping instrument 31, and a latch 43 is at the opposite end. In one embodiment, no latch is required as the handles can hold the instrument in the closed position when being held by a surgeon or surgeon's assistant. In another embodiment, a latching device can be provided on or associated with the handles as opposed to directly on the jaws of the clamping instruments.

As shown best in FIG. 6, the instrument 31 may accommodate the moment arms 21 at various angles in the inferior/superior plane. The resilient material 35 assists in this regard as it conforms to and grips the arms 21 at various angles. As shown, the instrument 31 may be also be used in a left-right orientation, and the moment arms 21a and 21d may be attached to pedicle screws on either side of the spinous process of the same vertebra. This arrangement creates a triangulated structure that can apply a greater torque to a vertebra while decreasing the bending moment on the pedicle screws. This approach can be used in conjunction with a second instrument 31 oriented in the superior-inferior direction to first create an initial alignment using the first instrument 31 and then restrain the vertebra with respect to other vertebrae using the second instrument 31.

FIG. 7 shows the clamping instrument 31 in an open position and more clearly shows portions of its structure, particularly the hinge and latching structures. In the preferred embodiment, a spring-loaded hinge biased toward the open position is employed. Also in a preferred embodiment, a spring-loaded ratchet and pawl type latch 43 is employed. Thus, one-handed operation is facilitated. The clamping instrument 31 can be arranged about the moment arms 21, i.e., extension tubes, closed and latched, all with one hand. Disengagement of the latch 43 is facilitated by the latch extension and finger grip which lies outside of one jaw. A simple depression of this extended finger grip portion will disengage the ratchet and pawl arrangement.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

We claim:

1. A system for direct vertebral rotation comprising:
   at least two levers, each of the levers being attachable to a pedicle screw implanted in a vertebra of a spine such that each lever extends proximally from the respective pedicle screw; and
   a clamping instrument configured to clamp the levers, the clamping instrument including a first jaw and a second jaw, each of the first and second jaws including an inner portion facing towards the other of the first and second jaws, the inner portion of each of the first and second jaws including a compliant material, wherein the first and second jaws are movable relative to one another to a closed position in which a plurality of the levers are receivable and alignable between the first and second jaws, and wherein the compliant material of the first and second jaws is configured to conform to at least a portion of the levers received between the first and second jaws when the first and second jaws are in the closed position.

2. The system of claim 1, wherein the clamping instrument comprises:
   a hinge connecting the first jaw and the second jaw;
   a lock for locking the first jaw to the second jaw; and
   handles attached to each of the first jaw and the second jaw, wherein the handles are configured to rotate the first jaw and the second jaw towards or away from each other.

3. The system of claim 1, wherein the clamping instrument includes handles configured to be held in a hand.

4. The system of claim 3, wherein the handles include a handle attached to each of the first and second jaws.

5. The system of claim 4, wherein each of the first and second jaws is elongated along a respective axis, and wherein each of the handles attached to the first and second jaws extends perpendicularly to the respective axis of the first and second jaws.

6. The system of claim 1, wherein the clamping instrument includes a hinge connecting the first jaw and the second jaw, and wherein the first and second jaws are rotatable relative to one another about the hinge.

7. The system of claim 1, wherein the clamping instrument includes a lock configured to latch the first and second jaws together in the closed position such that relative movement between the first and second jaws is restrained.

8. The system of claim 1, wherein the compliant material is made from a material selected from a group consisting of polymer and rubber.

9. The system of claim 1, wherein the compliant material of the inner portion of each of the first and second jaws defines a substantially planar surface facing towards the other of the first and second jaws.

10. The system of claim 9, wherein the substantially planar surfaces are substantially parallel to each other when the first and second jaws are in the closed position.

11. The system of claim 1, wherein the compliant material of one of the first and second jaws extends substantially parallel to the compliant material of the other of the first and second jaws when the first and second jaws are in the closed position.

12. The system of claim 1, wherein an elongate opening extending along the clamping instrument is defined between the first and second jaws when the first and second jaws are in the closed position, and wherein the compliant material of the inner portion of each of the first and second jaws extends longitudinally along substantially the entire length of the elongate opening.

13. The system of claim 1, wherein, when the first and second jaws are in the closed position, the compliant material of one of the first and second jaws is spaced apart from the compliant material of the other of the first and second jaws so as to define an opening therebetween, the opening being adapted to receive a plurality of the levers therein.

14. The system of claim 1, wherein the clamping instrument includes a hinge connecting the first jaw and the second jaw, the first and second jaws being rotatable relative to one another about the hinge, wherein the clamping instrument includes a lock configured to latch the first and second jaws together in the closed position such that relative movement between the first and second jaws is restrained, and wherein the lock is positioned at an opposite end of the first and second jaws from the hinge.

* * * * *